(12) United States Patent
Lipton

(10) Patent No.: US 7,091,329 B1
(45) Date of Patent: Aug. 15, 2006

(54) PROTEIN 68075 AND ITS USE FOR REGENERATING NERVE CELL PROCESSES

(76) Inventor: Stuart A. Lipton, 43 Peregrine, Newton, MA (US) 02159

( * ) Notice: Subject to any disclaimer, the term of this patent is extended or adjusted under 35 U.S.C. 154(b) by 0 days.

(21) Appl. No.: 08/346,910

(22) Filed: Nov. 30, 1994

Related U.S. Application Data

(63) Continuation of application No. 08/167,109, filed on Dec. 14, 1993, now abandoned, which is a continuation of application No. 07/932,926, filed on Aug. 20, 1992, now abandoned, which is a continuation of application No. 07/758,292, filed on Aug. 28, 1991, now abandoned, which is a continuation of application No. 07/619,653, filed on Nov. 27, 1990, now abandoned, which is a continuation of application No. 07/391,779, filed on Aug. 9, 1989, now abandoned.

(51) Int. Cl.
*C07H 21/04* (2006.01)
(52) U.S. Cl. ..................... 536/23.1; 536/23.5
(58) Field of Classification Search ............... 536/23.5, 536/23.1
See application file for complete search history.

(56) References Cited

U.S. PATENT DOCUMENTS 4,481,353 A 11/1984 Nyilas et al. ............... 528/303

OTHER PUBLICATIONS

Orlin et al. "Report and Recommendations of the Panel to loosen the NIH Investment in Research on Gene Therapy," NIH, pp. 1-40, 1995.*
Stull et al., *Pharmaceut. Research*, vol. 9, pp. 303-317, 1995.*
Jackowski, *Br. J. Neurosurg.*, vol. 9, pp. 303-317, 1995.*
Ullrich et al., *Nature*, vol. 303, pp. 821-825, 1983.*
Krainc et al., *Genomics*, vol. 29, pp. 809-811, 1995.*
Yoon et al. *Prog. news-Psychophasm & Biol. Psychiatry*, vol. 29 (2005), pp. 749-753.*
Spelites et al. *Neurosci.*, vol. 70, 1996, pp. 67-77.*
Kraine et al., *JBC*, vol. 273, 1998, pp. 26218-26224.*
Gubler, et al., "Simple and Very Efficient Method for Generating cDNA Libraries", 1983, *Gene*, 25:263-69.
Leifer et al., "A Monoclonal Antibody to Thy-1 Enhances Process Regeneration by Differentiated Rat Retinal Ganglion Cells In Culture", Soc. Neurosci., Abstract 9:6 (1983).
Leifer et al., "Monoclonal Antibody to Thy-1 Enhances Regeneration of Processes by Rat Retinal Ganglion Cells in Culture", Science, 224:303-306 (1984).
Lipton et al., "Regeneration of Processes and Electrophysiology of Rat Retinal Ganglion Cells in Culture", Invest. Opthalmol. Visual Sci., Supp. 24:138 (1983).
Mason et al., "The Kinetics of Antibody Binding to Membrane Antigens in Solution and at the Cell Surface", Biochem. J., 187:1-20 (1980).
Pillemer et al., "A Monoclonal Antibody that Detects a $V_k$-TEPC15 Idiotypic Determinant Cross-Reactive With a Thy-1 Determinant", 1981, *J. Exper. Med.*, 153:1068.
Williams et al., "Neuronal Cell Thy-1 Glycoprotein: Homoly with Immunoglobulin", Science, 216:696-703 (1982).

* cited by examiner

*Primary Examiner*—Janet L. Andres
*Assistant Examiner*—Stephen Gucker
(74) *Attorney, Agent, or Firm*—Fish & Richardson P.C.

(57) ABSTRACT

Purified human 68075, or a purified protein comprising at least a portion of the endogenous human 68075, is active in promoting regeneration of a central or peripheral neuron.

4 Claims, No Drawings

PROTEIN 68075 AND ITS USE FOR REGENERATING NERVE CELL PROCESSES

This application is a continuation under 37 CFR 1.78 of U.S. Ser. No. 08/167,109, now abandoned (hereby incorporated by reference), filed Dec. 14, 1993, which is a continuation of U.S. Ser. No. 07/932,926, filed Aug. 20, 1992, now abandoned, which is a continuation of U.S. Ser. No. 07/758,292, filed Aug. 28, 1991, now abandoned, which is a continuation of U.S. Ser. No. 07/619,653, filed Nov. 27, 1990, now abandoned, which is a continuation of U.S. Ser. No. 07/391,779, filed Aug. 9, 1989, now abandoned.

BACKGROUND OF THE INVENTION

This invention relates to methods for enhancing regeneration of mammalian nerve cells in vivo.

SUMMARY OF THE INVENTION

In a first aspect, the invention features a purified human protein, which we termed the 68075 protein, or a purified protein comprising a portion of the 68075 protein which is active in promoting regeneration of a process of a central or peripheral neuron. By "68075 protein" is meant the complete human protein having a portion encoded by the cDNA clone deposited with the American Type Culture Collection (ATCC) on Aug. 9, 1989 and assigned the Accession number 68075.

By "purified" is meant that the 68075 protein is isolated from its natural environment, e.g., a human cell, and one or more components with which it naturally occurs is reduced in level in comparison to the natural environment. It is preferred that 68075 be purified to the extent that it forms at least 10% of the protein of a preparation, and even more preferably that it forms the majority of the protein in that preparation. When used for treatment of humans, it is preferred that the 68075 protein be in the form of a homogeneous solution or lyophilized. That is, the 68075 protein is purified away from all compounds with which it naturally occurs. This term is meant to include purified naturally occurring 68075 polypeptide, but most preferably it refers to synthetic polypeptides forming the biologically active portion of 68075 (i.e., that portion able to promote regeneration of a neuron process), and molecules formed by recombinant genetic engineering techniques. Thus, the term includes polypeptides expressed within a bacterial, mammalian, or other cell, from a strand of DNA which does not naturally occur within that cell, or from DNA under the control of a regulatory sequence with which this DNA does not naturally occur.

The 68075 protein may be purified by a number of techniques. These include isolation of the naturally occurring polypeptide by immunoaffinity procedures using antibodies against the polypeptide, or anti-idiotypes (antibodies against 68075 antibodies). They also include isolation and purification of cells which naturally express, or are modified to express, high levels of the 68075 polypeptide. Such cells may be formed by genetic engineering techniques to introduce the 68075 gene, and manipulating the engineered cell to cause expression of that gene within the cell. It is also possible to insert secretion sequences, well known to those skilled in the art, upstream of the structural gene encoding 68075 to cause the polypeptide to be secreted into the medium surrounding the cells that then can be isolated from the medium.

The amino acid sequence of the part of the 68075 protein which is active in promoting regeneration of a process (e.g., an axon or a dendrite) of a central neuron may be determined by standard techniques, e.g., by expressing short fragments of the DNA encoding 68075 and determining which of the resulting polypeptides are active. This sequence of amino acids can be synthesized by standard chemical procedures well known to those skilled in the art. Such recombinant and synthetic peptides are within this invention.

Also included within the definition of polypeptide 68075 is 68075 which is caused to be produced in vivo within a human at a level at which it does not normally occur in that human cell. For example, agents which cause elevated production of 68075 may be administered to the human cells in order to elevate the level of 68075 expressed from the naturally occurring gene. Such agents can be identified by standard procedure using the cloned 68075 encoding gene and investigating the effect of agents on expression of the gene in vivo or in vitro. In addition, the naturally occurring gene may be modified by transfection of the cell with a virus in order to introduce a gene encoding a 68075, or an agent which modulates expression of the naturally occurring gene, to increase the level of expression of 68075 within that cell.

In a second aspect, the invention features purified nucleic acid encoding human 68075. This nucleic acid is separated from the environment in which it naturally occurs and is generally located on a vector, for example, a plasmid, cosmid, or phage, such that nucleic acid may be manipulated as desired. This nucleic acid includes not only nucleic acid which naturally occurs within a human cell, but modifications (made by standard procedures) of the nucleic acid which cause production of a 68075 protein identical in amino acid sequence to a naturally occurring 68075, or having one or more amino acids substituted or deleted without significantly affecting the biological activity of the resulting 68075 with regard to its promotion of the regeneration of a process of a central or peripheral neuron. Thus, the nucleotide bases within the nucleic acid may be substituted conservatively or non-conservatively using techniques well known to those skilled in the art. Similarly, nucleic acid closely related to naturally occurring human nucleic acid is encompassed by this invention. Such nucleic acid may be identified by using standard probe screening techniques, where the probe is a portion of at least 15–20 contiguous bases of the nucleic acid encoding human 68075. This probe nucleic acid is used under standard stringent hybridization conditions to identify nucleic acid homologous to that encoding the human 68075. Not all such homologous sequences will encode a 68075 protein, but those which do can be identified by standard procedures.

In a third aspect the invention features a method for promoting regeneration of a process of a neuron of a human. The method features providing the purified or recombinant human 68075 described above, and applying that protein to the neuron in an amount sufficient to promote regeneration of a process of a neuron of a human.

Some potential steps of providing and applying 68075 are briefly described above. These steps include provision of a homogenous preparation of 68075 protein directly to the neuron to be treated, or application of any other equivalent protein as defined above. Neurons which may be treated in this invention include those of the central nervous system, as well as the peripheral nervous system. Such treatment may include administering the substance in a nerve guide tube, well known to those skilled in the art, via an osmotic minipump, or by use of a slow release pellet, for example, an Elvax pellet. The protein may also be administered intrathecally, stereotactically or intravitreally (for CNS), or systemically (for PNS).

Alternatively, the level of 68075 protein within a cell may be increased by regulation of the naturally occurring 68075 gene within that cell, or of a gene which is introduced into the cell by a standard technique. For example, a viral promoter system (e.g., HSV-1 promoter) can be used to cause expression of 68075 in adult glial or other cells, e.g., nerve cells, which no longer, or do not naturally, express the 68075 protein, by insertion of that promoter upstream of the natural 68075 encoding gene. In addition, a cell line of autologous cells (e.g., glia or other cell types) encoding 68075 can be transfected with such a viral promoter to cause expression of the protein and these cells transplanted into the CNS or PNS. Fragments of cells or entire cells, e.g., young or passaged astrocytes that express 68075, can be introduced stereotactically into the nervous system.

Applicants have found that protein 68075 of mammals enhances the regeneration of nerve cell processes in vivo in humans. These proteins are useful in treatment of diseases caused by nerve cell degeneration, for example, dementia or other injury, and also for treatment for peripheral nerve degeneration or severance. For example, after operations known to produce male impotence, administration of 68075 protein at the cut site of the neuron will enhance regeneration of the neuron.

Other features of the invention will be apparent from the following description of the preferred embodiments and from the claims.

Description of the Preferred Embodiments 68075 Protein 68075 protein has been defined above. There follows an example of isolation of clone 68075 from human cells. Those skilled in the art will recognize that this example is not limiting to the invention and other methods for isolation of purified 68075 will be readily apparent upon reading of this disclosure. Similarly, the complete 68075 encoding gene can be readily isolated by standard techniques using the partial clones provided in this application. To this end, a deposit has been made of a clone including 500 bases encoding at least some of the 68075 polypeptide, and a clone including 1340 bases encoding nearly all of the 68075 polypeptide. These deposits have been made in the American Type Culture Collection, 10801 University Boulevard, Manassas, Va., 20110-2209, under the terms of the Budapest Treaty on the International Recognition of the Deposit of Microorganisms for the purpose of Patent Procedure. Applicant's assignee, Children's Medical Center Corporation of Boston, represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1.14 and 35 USC 112. The deposited material will be maintained with all the care necessary to keep it viable and uncontaminated for a period of at least five years after the most recent request for the furnishing of a sample of the deposited material, and in any case, for a period of at least thirty years after the date of deposit or for the enforceable life of the patent, whichever period is longer. Applicant's assignee acknowledges its responsibility to replace the deposit should the depository be unable to furnish a sample when requested due to the condition of the deposit. The first deposit is assigned the accession number 68075 and was deposited on Aug. 9, 1989. The second deposit was made on Nov. 30, 1994 and is assigned the accession number 75949 or 97525.

In the example to be described, anti-idiotypic antibodies to Thy-1 antibodies were used to screen a cDNA library of human DNA. The anti-idiotypic antibodies against Thy-1 antibodies were characterized by Pillemer et al. J. Experimental Medicine, 153:106, 1981, hereby incorporated by reference. These were obtained and purified according to the methods described by Pillemer et al. These anti-idiotypic antibodies are not essential to the present invention. Applicant believes that the anti-idiotypic antibodies used in the present invention are available from Pillemer et al, or commercially available from Sigma (St. Louis) or Hazelton Labs (PA).

The anti-idiotypic antibodies TEPC-15, HOPC-8, MOPC-603, and MOPC-167 of Pillemer et al. were purified from ascitic fluid over an anti-IgA affinity column. Media surrounding the cells was centrifuge-filtered and passed through an Amicon concentrator. This was stored at −80° until use. The ascitic fluid was then passed over an anti-IgA affinity column, and the eluate dialyzed and concentrated against 0.5 M NaCl, 0.1 M NaHCO$_3$.

Example 1 cDNA Encoding Part of Human 68075

A fetal human brain cDNA library was constructed in lambda gt11. To accomplish this, cDNA was synthesized from 10 mg of polyadenylated RNA by a modification of the method of Gubler et al., Gene 25:263, 1983. A double-stranded cDNA was treated with EcoR1 methylase, ligated to EcoR1 linkers, cleaved with EcoR1, and passed over a Sepharose CL4-B column to remove excess linkers. The cDNA was ligated to lambda gt11 DNA which had been pre-ligated, digested with 100-fold excess of EcoR1, and phosphatased using one unit of calf intestinal alkaline phosphatase (Boehringer Mannheim) per 70 mg of phage DNA. Approximately 500 ng of cDNA was ligated to 50 ng of lambda gt11 arms. The DNA was packaged according to standard protocols and amplified in $E.$ $coli$ Y 1088 on tryptone plates (1% Bacto-tryptone, 0.5% NaCl, 1.2% agar, 2 mM MgCl$_2$) in tryptone top agar (0.8% agar). To screen the library, the phage was grown on Y1090 at a density of 100,000 per 150 mm plate. Standard protocol was followed through incubation of the filters in the primary (anti-idiotype) antibodies in Tris buffer with 1% goat serum. Filters were then washed twice is Tris buffer containing 0.1% Triton X-100, incubated in peroxidase-conjugated goat anti-mouse IgA second antibodies, washed in 50 mM Tris, pH 7.4, and visualized with diaminobenzidine and hydrogen peroxide. A positive plaque was then cloned and used in a Northern blot analysis for hybridization to mouse RNA obtained from cultures of astrocytes.

A preliminary screening of the library using the anti-idiotype antibodies TEPC-15 and HOPC-8 revealed a single positive clone consisting of approximately 500 base pairs of cDNA, originally designated TR1, now called 68075$_{DNA}$.

Rescreening of the brain library with the 500 base clone identified two two kilobase (clones TR2A and TR2B (now accession number ATCC 97525) (SEQ. ID. NO.:1))) and three three kilobase (clones TR3A, TR3B, and TR3C) clones to which the 500 base clone hybridized. The mRNA detected on Northern blots with clone 68075$_{DNA}$ is 6 kb in size.

However, much of it, may consist of nontranslated sequences. In Western blots, 30–60 kDa bands were detected, suggesting that 68075 requires only about two kilobases to encode the full length protein.

The above clone, $68075_{DNA}$, is the cDNA included in ATCC Deposit No. 68075, and can be used to identify other candidate clones to insure that a full length 68075 clone is obtained. This clone may be manipulated by standard procedures to determine the DNA sequence of the clone, and thence the amino acid sequence of 68075. Once these sequences are determined, the 68075 gene can be manipulated into any standard expression vector to cause expression of the 68075 protein from any number of standard expression cells. The expressed 68075 protein is then isolated and purified by standard techniques. A 68075-encoding gene can also be transfected into mammalian cells, for example, by using recombinant clones in the DO vectors, such as DOL and/or DOJ, which contain the polyoma early region, or pBR322. These retrovirus constructs are used to overexpress the protein in a mammalian cell line that does not normally express 68075. For example, NIH 3T3 cells can be used. In this method a sodium phosphate buffer at pH 6.95 is mixed with a calcium DNA solution, and the calcium phosphate DNA precipitate formed allowed to precipitate gradually onto the cells to provide a high efficacy of stable transformation. Those cells transformed are expanded by standard procedure. An example of an eukaryotic expression library includes the pH3M vector, having an SV40 origin of replication, an M13 origin, a SupF marker, and a convenient cloning site. Cells expressing 68075 are selected by panning (e.g., by their adherence to dishes coated with anti-idiotypic antibody). DNA is isolated from adherent cells and used to transform MC1061/p3 cells, amplified, and used to transfect COS cells for a second round of enrichment. Standard methods can be used to produce variants of the DNA clones, which may include variants of 68075 at the amino acid level.

Example 2

Affinity Purification of 68075

68075 protein may be purified by affinity column purification. Either astrocyte cultures or whole brain preparations are solubilized in detergent (Nonidet P-40 or sodium deoxycholate), passed over the column, and then equilibrated with buffer (1M Tris HCl, pH 7.4). Elution of 68075 is with acidic and basic buffers (e.g., 0.1 M glycine HCl, pH 2). The resulting fractions are assayed for protein, and those fractions containing protein assayed for 68075. 68075 is identified by standard SDS polyacrylamide gel electrophoresis, or by immunoblot analysis. Alternatively, anti-idiotypic antibodies such as those discussed above, or monoclonal antibodies to 68075, may be used in its detection.

Methods

In order to use the above described 68075, any number of methods may be utilized as discussed above.

Example 3

Promotion of Regeneration with 68075.

One method of this invention includes providing a supply of 68075 protein immobilized on a solid support. This support is placed in proximity to a mammalian neural process in a living mammal to promote growth and regeneration of the process. The method of the invention is particularly applicable to neural processes including ganglion cell bodies, such as retinal ganglion cell bodies, but can also be used to enhance regeneration of nerve cell processes in the peripheral as well as the central nervous system.

The term "solid support" includes both rigid materials such as glass, synthetic plastics, and the like on the surface of which a layer or coating of the monoclonal antibody is bonded, and also soft gels penetrable by the regenerating nerve process such as collagen, fibrin, fibrinogen, blood clot, or laminin throughout which the monoclonal antibody is dispersed and bonded so that it is immobilized. A supply of 68075 immobilized in a soft gelatinous mass such as a proteinaceous gel, for example collagen gel, enclosed within an open ended tube or hollow cylinder of glass or synthetic plastic which serves as a guide for the regenerating processes, the latter advancing through the center of the tube, can also be used. The synthetic plastic used for the tube or hollow cylinder can be any nontoxic material to which antibodies bond, such as polyethylene, polypropylene, etc., but is preferably a bioresorbable material such as that described in Nyilas, U.S. Pat. No. 4,481,353. The guide filled with proteinaceous gel on which 68075 is immobilized is implanted so as to bridge the gap between the ends of a damaged or severed process to enhance regeneration and extension of the process through the center of the tube spaced from the synthetic plastic wall. The following example is intended to illustrate more fully the nature of the invention without acting as a limitation upon its scope. It is understood that this example demonstrates the utility of 68075 in rats but that naturally or traumatically induced defects in neural processes can also be treated in this manner.

Male Sprague-Dawley rats can be utilized in these studies. Four animals serve as an unoperated control and three animals receive an intracranial optic nerve transection alone. In eight animals, one optic nerve is transected intracranially and then a nerve guide tube implanted to bridge the transected nerve. To achieve this, a small craniotomy is made in the frontal lobe and carefully aspirated to expose a 2 to 3-mm segment of one optic nerve intracranially. The pial plexus of capillaries together with the anterior cerebral artery are gently retracted medially and the nerve transected. Such an intracranial nerve transection spares the blood supply to the retina.

After hemostasis is achieved, a 1.5-mm length (0.95 mm o.d, 0.75 mm i.d.) of the nerve guide is inserted. The nerve guides used in these experiments are fabricated as polymers of synthetic poly D,L-lactates with 2% triethyl citrate as a plasticizer, as described in U.S. Pat. No. 4,481,353.

The experimental animals are divided into three groups. In one group (two rats), empty nerve guide tubes are implanted. In the second group (three rats), the nerve guides' lumen is filled with a collagen matrix (Vitrogen, Flow Laboratories, diluted in 0.1 M phosphate buffer to a final concentration of 2.48 mg/ml) containing a 0.5 mg/ml fibrinogen (bovine, CalBiochem) immediately before implantation. The third group (three rats) receive nerve guides containing 68075, in addition to the collagen and fibrinogen.

In all animals, both the proximal and distal nerve stumps are inserted into the guide. At the time the nerve guides are implanted, all experimental animals receive bilateral superior cervical ganglionectomies to remove the sympathetic innervation to the head. This procedure is necessary to rule out the ingrowth of peripheral sympathetic fibers, a process which has been shown to occur after indirect and direct lesions to the CNS.

Four weeks postoperatively the animals are deeply anesthetized and perfused through the heart with 200 ml heparinized saline, followed by 500 ml 1% paraformaldehyde plus 3% glutaraldehyde, followed by 200 ml 0.1 M phosphate buffer. All perfusion solutions are made up in 0.1 M phosphate buffer. The nerve guide is dissected out as one piece, immersed in 1% osmium tetroxide, and processed for embedding in plastic (DER, Ted Pella, Inc.). One micrometer transverse sections are cut from the proximal, middle, and distal portions of the nerve guide and stained with toluidine blue. "Proximal" refers to sections across the part of the nerve guide closest to the eye.

Data are collected with a computer-controlled light microscope at a final magnification of 1600×. Blood vessels are identified and their luminal profiles entered on-line from a digitizing tablet to a display terminal and then to a VAX 11/780 computer (Digital Equipment Corp.) for further numerical and statistical analysis. For each cross-sectioned sample the tissue cable areas, the number of blood vessels, and the area of each blood vessel is obtained. This data allows determination of whether the 68075 is active in promoting neural process growth.

This procedure can also be used to determine the use of various forms of 68075, or fragments thereof. For example, recombinant 68075 can be expressed by standard procedure and tested for its efficacy in this method. By expression of parts of the 68075-encoding DNA that portion having the desired activity in this assay can readily be determined.

One other method for measuring the use of 68075 for neuronal regeneration is the retinal culture procedure of Leifer et al, 1984, supra. Generally, rat and mouse retinal ganglion cells are identified with fluorescent dyes that are retrogradely transported to the ganglion cell bodies after injection into the superior colliculus and lateral geniculate body, to which the ganglion cells project. Fluorescently-tagged Thy-1 antibodies are specific among retinal cells in vitro for the ganglion cells. Double labelling experiments show virtually complete overlap between the two marking methods, ensuring the validity of either for identifying the ganglion cells. Ganglion cells are dissociated from the retinas of 4 day-old to adult rats or mice under anesthesia using papain (10 units/ml, Cooper Biomedical, Inc.) and mild mechanical trituration. The dissociated retinal cells are plated in culture using minimal essential media and 5% rat serum (for rat cultures) or fetal calf serum (for mouse cultures). For rat cultures, Long-Evans rats are used, and, for mouse cultures, C57BL/6 mice.

To measure the regeneration of processes by the ganglion cells, retinal cells from a single dissociation are cultured with and without 68075 in multiple dishes (each receiving a 50 μl drop of the same dilution of cells). On the second, third, and fourth days in culture, solitary ganglion cells are measured for the diameter of the soma, and each process is measured using a computer graphics system.

OTHER EMBODIMENTS

Other embodiments are within the following claims.

What is claimed is:

1. An isolated nucleic acid comprising Clone ATCC 97525 (SEQ. ID. NO.:1).

2. An isolated nucleic acid comprising Clone ATCC 68075.

3. An isolated nucleic acid comprising Clone ATCC 75949.

4. An isolated fragment of the nucleic acid of clone ATCC 68075 comprising at least 20 contiguous bases.

* * * * *

UNITED STATES PATENT AND TRADEMARK OFFICE
CERTIFICATE OF CORRECTION

PATENT NO. : 7,091,329 B1  
APPLICATION NO. : 08/346910  
DATED : August 15, 2006  
INVENTOR(S) : Stuart A. Lipton Page 1 of 1

It is certified that error appears in the above-identified patent and that said Letters Patent is hereby corrected as shown below:

Title page, (56) References Cited, OTHER PUBLICATIONS, first column, at the Stull et al. reference, "vol. 9, pp. 303-317" should be -- vol. 12, pp. 465-483 --.

Title page, (56) References Cited, OTHER PUBLICATIONS, second column, at the Yoon et al. reference, "news-Psychophasm" should be -- Neuro-Psychophasm --.

Column 4, line 64, before "97525" insert -- 75949 or --.

Signed and Sealed this

Eighteenth Day of December, 2007

JON W. DUDAS
*Director of the United States Patent and Trademark Office*

SEQUENCE LISTING

<160> NUMBER OF SEQ ID NOS: 1

<210> SEQ ID NO 1
<211> LENGTH: 1341
<212> TYPE: DNA
<213> ORGANISM: Homo sapiens

<400> SEQUENCE: 1

```
aaaacgggga ctatggggag aaaaaagatt cagattacga ggattatgga tgaacgtaac      60
agacaggtga catttacaaa gaggaaattt gggttgatga agaaggctta tgagctgagc     120
gtgctgtgtg actgtgagat tgcgctgatc atcttcaaca gcaccaacaa gctgttccag     180
tatgccagca ccgacatgga caaagtgctt ctcaagtaca cggagtacaa cgagccgcat     240
gagagccgga caaactcaga catcgtggag acgttgagaa agaagggcct taatggctgt     300
gacagcccag accccgatgc ggacgattcc gtaggtcaca gccctgagtc tgaggacaag     360
tacaggaaaa ttaacgaaga tattgatcta atgatcagca ggcaaagatt gtgtgctgtt     420
ccacctccca acttcgagat gccagtctcc atcccagtgt ccagccacaa cagtttggtg     480
tacagcaacc ctgtcagctc actgggaaac cccaacctat tgccactggc tcacccttct     540
ctgcagagga atagtatgtc tcctggtgta acacatcgac ctccaagtgc aggtaacaca     600
ggtggtctga tgggtggaga cctcacgtct ggtgcaggca ccagtgcagg gaacgggtat     660
ggcaatcccc gaaactcacc aggtctgctg gtctcacctg gtaacttgaa caagaatatg     720
caagcaaaat ctcctccccc aatgaattta ggaatgaata accgtaaacc agatctccga     780
gttcttattc caccaggcag caagaatacg atgccatcag tgtctgagga tgtcgacctg     840
```

```
                                                      -continued
cttttgaatc aaaggataaa taactcccag tcggctcagt cattggctac cccagtggtt   900
tccgtagcaa ctcctacttt accaggacaa ggaatgggag gatatccatc agccatttca   960
acaacatatg gtaccgagta ctctctgagt agtgcagacc tgtcatctct gtctgggttt  1020
aacaccgcca gcgctcttca ccttggttca gtaactggct ggcaacagca acacctacat  1080
aacatgccac catctgccct cagtcagttg ggagcttgca ctagcactca tttatctcag  1140
agttcaaatc tctccctgcc ttctactcaa agcctcaaca tcaagtcaga acctgtttct  1200
cctcctagag accgtaccac cacccttcg agatacccac aacacacgcg ccacgaggcg   1260
gggagatctc ctgttgacag cttgagcagc tgtagcagtt cgtacgacgg gagcgaccga  1320
gaggatcacc ggaacgaatt c                                            1341
```